(12) United States Patent
Lueken et al.

(10) Patent No.: US 8,846,994 B2
(45) Date of Patent: Sep. 30, 2014

(54) METHOD FOR PRODUCING LOW-ODOR N-BUTANE

(75) Inventors: Hans-Gerd Lueken, Marl (DE); Alfred Kaizik, Marl (DE); Markus Winterberg, Datteln (DE); Wilfried Bueschken, Haltern am See (DE); Dirk Fridag, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/381,735

(22) PCT Filed: May 21, 2010

(86) PCT No.: PCT/EP2010/057031
§ 371 (c)(1),
(2), (4) Date: Feb. 16, 2012

(87) PCT Pub. No.: WO2011/000633
PCT Pub. Date: Jan. 6, 2011

(65) Prior Publication Data
US 2012/0136186 A1    May 31, 2012

(30) Foreign Application Priority Data
Jul. 1, 2009  (DE) .......................... 10 2009 027 406

(51) Int. Cl.
C07C 5/00 (2006.01)
C07C 9/10 (2006.01)
C07C 7/163 (2006.01)
C07C 7/10 (2006.01)

(52) U.S. Cl.
CPC . *C07C 9/10* (2013.01); *C07C 7/163* (2013.01); *C07C 7/10* (2013.01)
USPC ........... 585/250; 585/800; 585/802; 585/833; 585/836; 585/853; 585/854; 208/263; 208/273; 208/255; 208/256; 208/258; 208/259; 208/270; 208/271; 208/283; 208/284; 208/286; 568/451; 568/454

(58) Field of Classification Search
CPC .............. C07C 5/00; C07C 5/02; C07C 5/03; C07C 45/49; C07C 45/50; C07C 45/505; C07C 7/00; C07C 7/005; C07C 7/04; C07C 7/10; C07C 7/163; C07C 7/167; C10G 19/00; C10G 19/02; C10G 19/08
USPC ......... 585/250, 800, 802, 833, 836, 853, 854; 208/255, 256, 258, 259, 263, 271, 273, 208/283, 284, 286; 568/451, 454
See application file for complete search history.

(56) References Cited

U.S. PATENT DOCUMENTS 5,191,149 A * 3/1993 Kulkarni ........................ 585/802
6,037,516 A * 3/2000 Morford et al. ............... 585/836

(Continued)

FOREIGN PATENT DOCUMENTS

DE  10 2007 061 649   7/2009
DE  10 2008 002 187   12/2009

(Continued)

OTHER PUBLICATIONS

U.S. Appl. No. 13/502,226, filed Apr. 16, 2012, Kaizik, et al.

(Continued)

*Primary Examiner* — In Suk Bullock
*Assistant Examiner* — Philip Louie
(74) *Attorney, Agent, or Firm* — Oblon, Spivak, McClelland, Maier & Neustadt, L.L.P.

(57) ABSTRACT

The invention relates to a method for producing low-odor n-butane by catalytic hydrogenation of a feed mixture. The aim of the invention is to provide such a method, wherein the feed material, in addition to n-butane, n-butene and up to 1 mass % formic acid and/or up to 1 mass % pentanals and/or up to 0.5 mass % pentanols, also comprises carbon monoxide. The aim is achieved by treating the feed mixture in the temperature range of 15 to 120° C. with an aqueous solution of an alkali metal or alkaline earth metal hydroxide in the concentration range of 0.5 to 30 mass % and subsequently subjecting the feed mixture to the catalytic hydrogenation.

20 Claims, 2 Drawing Sheets

(56) References Cited

U.S. PATENT DOCUMENTS

Figure 1:
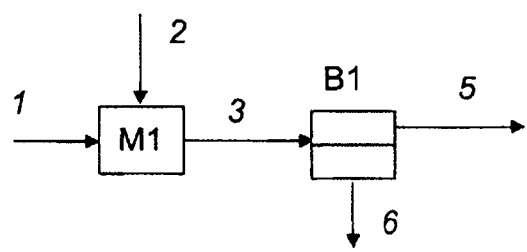

| | | | |
|---|---|---|---|
| 6,680,414 B2 | 1/2004 | Knoop et al. | |
| 7,361,714 B2 | 4/2008 | Grass et al. | |
| 7,524,997 B2 | 4/2009 | Kaizik et al. | |
| 8,143,468 B2 | 3/2012 | Kaizik et al. | |
| 2003/0153791 A1 | 8/2003 | Richter et al. | |
| 2006/0041167 A1 | 2/2006 | Grass et al. | |
| 2007/0135665 A1 | 6/2007 | Wiese et al. | |
| 2007/0149839 A1* | 6/2007 | Rix et al. | 585/664 |
| 2007/0161829 A1* | 7/2007 | Van Driessche | 568/883 |
| 2009/0023882 A1* | 1/2009 | Hanefeld et al. | 526/348.7 |
| 2011/0060169 A1 | 3/2011 | Kaizik et al. | |

FOREIGN PATENT DOCUMENTS

| | | |
|---|---|---|
| WO | 99 26937 | 6/1999 |
| WO | 02 00582 | 1/2002 |
| WO | 2011 045102 | 4/2011 |

OTHER PUBLICATIONS

U.S. Appl. No. 13/808,010, filed Jan. 2, 2013, Boeing, et al.

International Search Report Issued Jul. 21, 2010 in PCT/EP10/057031 filed May 21, 2010.

Combined Office Action and Search Report issued Oct. 10, 2013 in Chinese Patent Application No. 201080029592.X with English language translation.

Xu Ze-hui, et al., Catalytic activity of N i/$Al_2O_3$-$SiO_2$ catalyst for hydrogenation of mono-olefins in $C_4$ fraction, Journal of Fuel Chemistry and Technology, vol. 34, No. 1, Feb. 2006, pp. 42-46 with English abstract and partial English translation.

Office Action issued Apr. 8, 2014, in Chinese Patent Application No. 201080029592.X, filed May 21, 2010 (with English-language Translation).

* cited by examiner

METHOD FOR PRODUCING LOW-ODOR N-BUTANE

The present invention relates to a process for preparing low-odour n-butane by catalytically hydrogenating a starting mixture.

Low-odour n-butane is used as an aerosol propellant. For this use, the n-butane must not have any additional components with troublesome odour. Apart from the faint intrinsic odour of n-butane, no further odour must be perceptible.

Low-odour n-butane can be prepared by hydrogenating n-butane/n-butene mixtures which comprise traces of polyunsaturated hydrocarbons such as butadiene and/or may have small amounts of $C_5$ hydrocarbons. The catalysts used for the hydrogenation are preferably supported noble metal catalysts, for example palladium on alumina support.

Such starting streams could, for example, be raffinate II or raffinate III. For economic reasons, however, preference is given to using mixtures of linear $C_4$ hydrocarbon streams consisting principally of n-butane.

A starting mixture used for the preparation of low-odour n-butane is the residual stream which remains in the oligomerization of the linear butenes of raffinate II or raffinate III after removal of the oligomer. This residual stream consists solely of hydrocarbons.

If, in contrast, a mixture of linear $C_4$ hydrocarbons, for example raffinate II or raffinate III, is hydroformylated, after removal of synthesis gas and hydroformylation products, an n-butane-rich mixture of linear $C_4$ hydrocarbons is present, which contains small amounts of formic acid, $C_5$ aldehydes and possibly $C_5$ alcohols, possibly synthesis gas, and water.

For the following reasons, low-odour n-butane can be obtained from such mixtures by hydrogenation and possible distillation only at a high level of cost and inconvenience: the formic acid forms carbon monoxide over the hydrogenation catalyst, which impairs the hydrogenation performance thereof, and so hydrogenation of olefins in the trace range can be achieved only by means of low catalyst hourly space velocities. Pentanals are hydrogenated for the most part to pentanols. Both pentanols and pentanals, even in the trace range, are impermissible for n-butane for aerosol applications.

Furthermore, formic acid even in the trace range is very corrosive, and so use of inexpensive unalloyed materials for the apparatus is impossible. Due to the corrosive effect of formic acid, the capital costs rise since highly alloyed steels have to be used.

WO 99/26937 discloses washing formic acid out of a hydrocarbon mixture with the aid of sodium hydroxide solution. However, if the starting mixture also comprises carbon monoxide in addition to the hydrocarbons, the process disclosed therein is unsuitable for removing formic acid: this is because reaction of carbon monoxide with sodium hydroxide solution additionally forms salts of formic acid, which runs counter to the purification desired. The process described in WO 99/26937 is therefore unsuitable for performance in the presence of carbon monoxide.

In the light of this prior art, it is an object of the present invention to specify a process for preparing low-odour n-butane by catalytically hydrogenating a feedstock, wherein the feedstock comprises, in addition to n-butane, n-butene and up to 1% by mass of formic acid and/or up to 1% by mass of pentanals and/or up to 0.5% by mass of pentanols, also additionally carbon monoxide.

This object is achieved by a process according to Claim 1. Preferred developments of the invention are laid down in the dependent claims.

The invention is therefore based on the finding that it is possible to prepare low-odour n-butane from a carbon monoxide-containing n-butane/n-butene mixture containing small amounts of formic acid and/or pentanals and/or pentanols by catalytic hydrogenation with hydrogen when the starting mixture before the hydrogenation is treated with an aqueous solution of an alkali metal hydroxide or alkaline earth metal hydroxide while maintaining the reaction parameters according to the claims. The treatment of the $C_4$ stream with alkali binds the formic acid as a salt. Pentanals form aldol addition or aldol condensation products. Pentanols remain dissolved in the alkali. Inventive treatment with alkali additionally also removes carbon monoxide from the starting mixture, and so damage to the catalyst in subsequent hydrogenation is avoided.

The process according to the invention also the following advantages on: the capital investment for an apparatus for removal of the troublesome components from the n-butane/n-butene mixture is low. The operating costs for this removal are small. The removal of the formic acid reduces the costs of the hydrogenation catalyst. Furthermore, the risk of corrosion by formic acid is reduced, and so inexpensive steels can be used for the construction of the plants downstream of the alkali wash, for example distillation columns, heat exchangers and hydrogenation plant.

The overall process for preparing for preparing the low-odour n-butane consists of the sequence of four process types, namely base extraction, dewatering by distillation, hydrogenation of the olefins and optional distillative removal of $C_5$ hydrocarbons. The present invention relates to the base extraction. The sequence of the three other steps can optionally be amended.

The present invention is described in detail hereinafter.

Feedstocks for the process according to the invention are carbon monoxide-containing mixtures of n-butane and linear butenes, which contain formic acid and/or pentanal(s) and/or pentanols as secondary component(s). The content of linear butenes in these mixtures is preferably below 30% by mass, especially below 15% by mass, very particularly below 10% by mass. In addition, these mixtures may contain polyunsaturated hydrocarbons, for example 1,3-butadiene, and up to 1.5% by mass of $C_5$ hydrocarbons. The formic acid content is in the range from 0.001 to 1% by mass, especially in the range from 0.001 to 0.1% by mass, very particularly in the range from 0.005 to 0.010% by mass. The content of pentanals is 0.001 to 1% by mass, especially 0.001 to 0.5% by mass, very particularly 0.005 to 0.010% by mass. The range of pentanols is in the range from 0.001 to 0.5% by mass, especially in the range from 0.001 to 0.2% by mass, very particularly in the range from 0.01 to 0.1% by mass. The carbon monoxide content in the starting mixture is in the range from 1 to 10% by mass. In addition, the starting mixture may comprise molecular hydrogen. The starting mixture may be monophasic or biphasic, for instance with a liquid phase and a gas phase. The carbon monoxide may be gaseous and/or at least partly dissolved in the liquid phase. Of the total amount of the carbon monoxide, more than 90% is in gaseous form.

Typical feedstocks for the process according to the invention are n-butane/n-butene mixtures which are obtained in the workup of product outputs of a hydroformylation of linear butenes. Such a process is described, for example, in DE 10 2008 002187.3. In this process, an n-butene/n-butane mixture is hydroformylated. The products and unconverted reactant are carried out of the reactor with excess synthesis gas. This gas stream is separated into synthesis gas, products (pentanals and conversion products) and an n-butane/n-butene mixture.

According to the method of distillative workup, a gaseous, liquid or both gaseous and liquid product mixture can be removed.

In the case of distillative separation in the pressure range from 0.5 MPa to 3.0 MPa, preferably both a liquid product stream in which synthesis gas is dissolved and a synthesis gas stream with a high proportion of $C_4$ compounds are obtained.

Both the liquid stream and the gaseous stream can be worked up separately or together by the process according to the invention.

According to the invention, troublesome components such as formic acid and/or pentanals and/or pentanols are removed from the n-butane/n-butene mixtures by treatment with an aqueous alkali.

The alkalis used may be aqueous solutions of alkali metal hydroxide or alkaline earth metal hydroxide. Preference is given to using sodium hydroxide solution and potassium hydroxide solution, especially sodium hydroxide solution.

The concentration of the hydroxides in the aqueous solution is 0.5 to 30% by mass, especially 2 to 5% by mass. In the case of sodium hydroxide solution, the sodium hydroxide content is preferably in the range from 0.5 to 25% by mass, especially in the range from 1 to 5% to mass, very particularly in the range from 2.5 to 3.5% by mass.

The treatment with alkali converts the formic acid present in the starting mixture to the corresponding formate. Pentanals form principally aldol addition and/or aldol condensation products which have a lower vapour pressure than the pentanals. Formates, conversion products of the pentanals and also pentanols are soluble in the aqueous phase.

The alkali wash thus effects both a chemical conversion and an extraction of the troublesome components or conversion products thereof into the aqueous phase.

The alkali wash can be performed in one or more reactor(s) with a downstream apparatus for phase separation.

Preference is given to effecting the alkali treatment in an extraction apparatus. It is possible to use the extraction apparatus known to those skilled in the art, for example simple extraction columns, sieve tray columns, columns with random packing or columns with moving internals. Examples of extraction apparatuses with moving internals include the rotary disk extractor and the Scheibel column. A further apparatus, which is used especially at high throughputs for the extraction, is what is called the mixer-settler-extractor. It is also possible to combine two or more extractors of identical or different design.

Since both the chemical reaction and an extraction of the troublesome components or conversion products thereof into the aqueous phase proceed very rapidly, only few theoretical plates are required for complete purification of the n-butane/n-butene mixtures. Therefore, the removal of the troublesome components in the process according to the invention is more preferably effected in a one-stage mixer-settler-extractor.

The mixers used may, for example, be injectors, centrifugal pumps, airlift pumps, mechanical stirrers or else static mixers, in which the organic phase and the alkali are mixed intimately. In the process according to the invention, preference is given to using static mixers or mixing pumps, especially centrifugal pumps.

The settlers used may be settlers which enable phase separation with sole utilization of gravity. These are called gravitational settlers and can also be configured with internals as a coalescence-promoting measure to increase the separating performance. The coalescence aids used may, for example, be plates, random packings, fabric packings or fibre bed settlers. Gravitational settlers may be configured as horizontal vessels or as upright vessels. As an alternative to gravitational settlers, for liquid-liquid separation from separators by the centrifuge principle can be used. Centrifugal forces in a rotating drum remove the heavy phase. In the process according to the invention, preference is given to using gravitational settlers configured as horizontal vessels with internals.

If both a liquid and a gaseous stream are to be purified, the mixer may have a downstream gas scrubber in which the gas stream is conducted in countercurrent to the liquid phase. Preference is given to using a column with random packing, in which the liquid phase is introduced to the upper third of the column and the gas stream to the lower third of the column. The gas phase is drawn off in the upper third of the column, above the introduction of the liquid, and the liquid phase is drawn off in the lower third of the column, below the introduction of the liquid phase. The liquid phase from the gas scrubber is then supplied to the settler, in which the separation between organic and aqueous phase is effected.

The alkali phase is supplied to the extraction in straight pass or preferably with recycling (cycle mode). The formate concentration in the extract (absorber phase leaving extraction) is below 0.2% by mass, especially below 0.1% by mass, very particularly below 0.05% by mass. If the alkali used is sodium hydroxide solution, the extract contains less than 0.2% by mass of sodium formate, especially less than 0.1% by mass, very particularly less than 0.01% by mass. The concentration of aldol addition and/or aldol condensation products in the pentanals in the extract is below the maximum solubility thereof in the alkali. The concentration of these pentanal conversion products in the extract is below 0.5% by mass, especially below 0.2% by mass. The concentration of pentanols in the extract is below 0.5% by mass. In the case of circulation mode, accordingly, the concentrations of the absorber phase in the upper column feed are limited such that the abovementioned limits are not exceeded. The throughput ratio (mass/mass) between n-butene/n-butane phase and alkali is between 30:1 and 2:1, preferably between 15:1 and 5:1.

The extraction is at temperatures between 15 and 120° C., especially between 40 and 90° C., very particularly between 60 and 80° C. The pressure in the extraction corresponds at least to the partial water pressure of the alkali.

In the preferably liquid removal of at least a portion of the raffinate, the pressure in the extraction is above the vapour pressure of the n-butane at extraction temperature. Since the extraction is preferably followed by a distillative workup, it is appropriate to perform the extraction at a higher pressure than the distillation in order to dispense with an intermediate compression. The pressure in the extraction apparatus is preferably in the range from 0.5 to 5.0 MPa, especially in the range from 1.5 to 3.0 MPa.

If sodium hydroxide solution is used for extraction, the extract (laden alkali) can be used as a catalyst for the aldol condensation of pentanals.

The raffinate consists principally of n-butane. It contains 1 to 30% by mass of n-butenes, especially 5 to 15% by mass. The formic acid content is below 5 ppm by mass, especially below 3 ppm by mass, very particularly below 1 ppm by mass. The content of oxygen-containing $C_5$ components, especially pentanals, is below 1 ppm by mass. As a result of the physical solubility of water in the organic phase at extraction temperature and pressure, the raffinate contains small amounts of water. In addition, the raffinate may contain $C_5$ hydrocarbons. If a gaseous raffinate phase also occurs, this consists principally of synthesis gas which comprises the abovementioned components in accordance with their partial pressures.

The raffinate (liquid and gaseous components) is separated by distillation into hydrocarbons (principally $C_4$ hydrocarbons, water and gases (principally synthesis gas)). The separation is effected in at least one column, preferably in exactly one column. The distillation column is provided with a top condenser and a phase separation vessel. During the distillation, the vapours are (partially) condensed and separated in the separation vessel into two liquid phases, namely a hydrocarbon phase and a water phase, and optionally into a gas phase. The aqueous phase and, if present, the gaseous phase are discharged. The bottom product obtained is a virtually anhydrous and gas-free hydrocarbon stream. The organic phase from the separation vessel is recycled into the upper part of the column.

The distillation column has preferably 5 to 45 theoretical plates, preferably 8 to 32 and more preferably 12 to 22 theoretical plates.

The feed to the column is preferably added between plates 1 and 16 (from the top), more preferably between plates 1 and 5. The ratio of feed rate supplied to vapour rate is, depending on the number of plates implemented, the water concentration of the column feed and the required purities of the bottom product, preferably less than 5, more preferably less than 1. The operating pressure of the column may preferably be set between 0.6 and 4.0 MPa (abs), preferably between 1.0 and 3.0 MPa (abs), more preferably between 1.5 and 2.5 MPa (abs).

The gas phase drawn off from the separating vessel consists principally of synthesis gas, which comprises hydrocarbons (principally $C_4$ hydrocarbons) in accordance with the partial pressures thereof and water. This gas mixture can be partly conducted (back) into a $C_4$ hydroformylation plant. It can be utilized as a heating gas, raw material for a synthesis gas plant, or to obtain hydrogen.

The bottom product of the distillation column consists to an extent of more than 99.90, especially to an extent of more than 99.95%, of hydrocarbons. The water content is below 20 ppm, preferably below 10 ppm, more preferably below 1 ppm.

According to the invention, the hydrogenation is effected in the presence of hydrogen. Hydrogen is used in a superstoichiometric amount. The hydrogen excess is preferably 5 to 20%.

The complete hydrogenation of the olefins in the bottom product, catalytically with hydrogen, can be performed continuously or batchwise in the gas or liquid phase.

According to the prior art, the hydrogenation is preferably undertaken in industry over fixed bed catalysts in the liquid phase.

The catalysts used may in principle be all catalysts known from the literature for the hydrogenation of olefinic double bonds. These are especially catalysts which contain nickel, palladium or platinum as hydrogenation-active metals.

For the hydrogenation, preference is given to using supported palladium catalysts. Preference is given to using supported catalysts containing 0.5 to 1.0% by mass of palladium on high-surface area γ-aluminas.

The hydrogenation is performed in the liquid phase within the temperature range from 20 to 140° C., especially within the temperature range from 40 to 100, very particularly within the temperature range from 30 to 60° C. The pressure in the hydrogenation apparatus is above the vapour pressure of n-butane. The pressure is preferably between 0.6 and 3 MPa, especially between 1 and 2 MPa.

The hydrogenation can be performed in one or preferably in more than one reactor(s). When the hydrogenation is undertaken in two reactors connected in series, the first is preferably operated in loop mode and the second in straight pass.

The hydrogenation output contains less than 1000 ppm by mass of olefins, preferably less than 500 ppm by mass of olefins, more preferably less than 200 ppm by mass.

Optionally, small amounts of $C_5$ hydrocarbons and dissolved hydrogen can be removed by distillation from the hydrogenation output in a further column.

Figure 2:
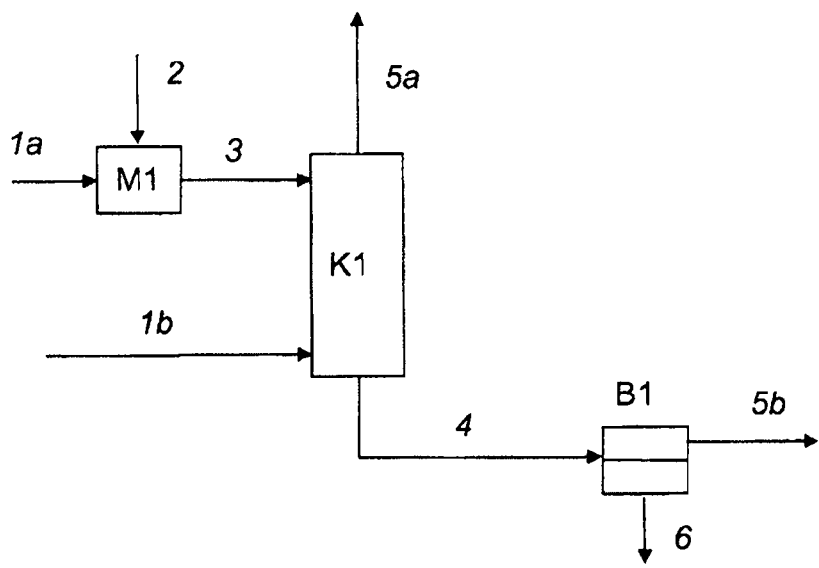
Figure 3:
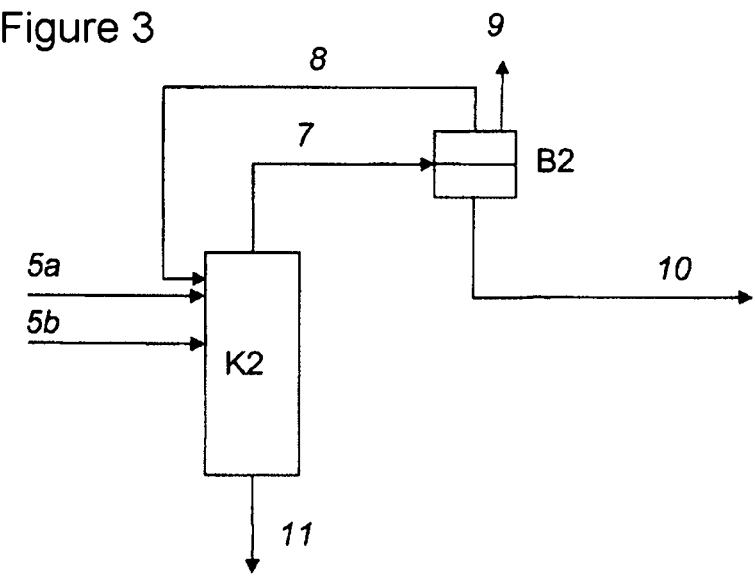
Figure 4:
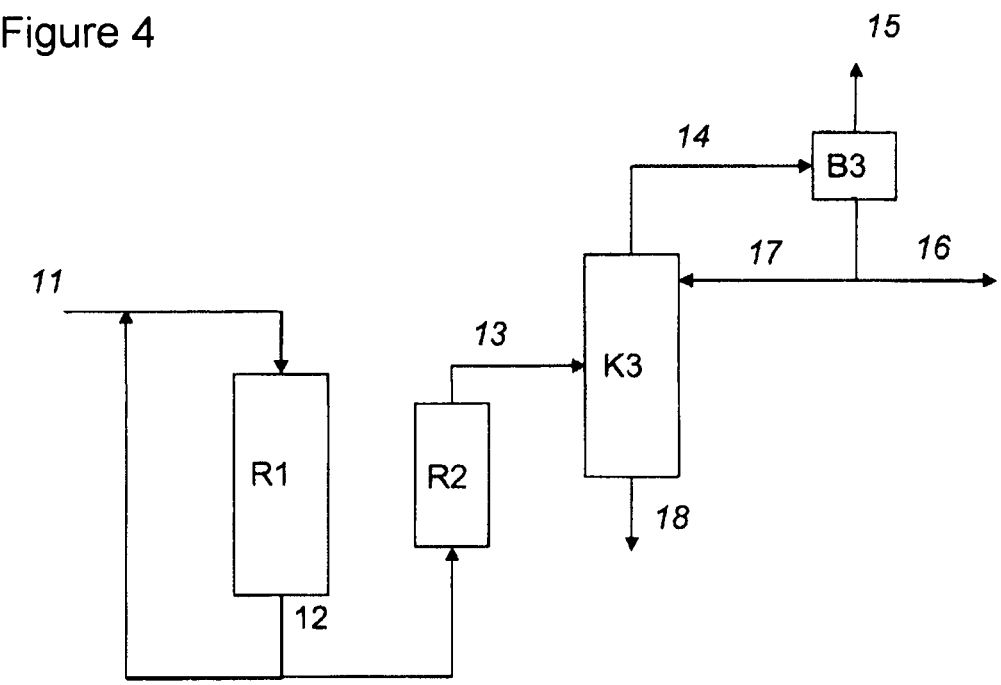

The invention will now be illustrated with reference to plant circuit diagrams. For this purpose, the figures show:

FIG. 1 plant for inventive alkali extraction for treatment of liquid starting mixtures;

FIG. 2 plant for inventive alkali extraction for treatment of biphasic starting mixtures;

FIG. 3 plant for distillative dewatering;

FIG. 4 plant for hydrogenation of the olefin stream and for distillative removal of $C_5$ hydrocarbons.

FIG. 1 shows the inventive extraction in the case that the starting mixture is exclusively in liquid form. The starting mixture comprising carbon monoxide, n-butane, n-butenes, small amounts of formic acid and oxygen-containing $C_5$ compounds is supplied to the mixer M1 and mixed therein with the extraction alkali (2). The biphasic mixture (3) is supplied to the settler B1. In the settler B1, the phases are separated, and the extract (6) is discharged as an aqueous phase laden with the impurities to be removed. A portion of the extract (6) can optionally be recycled as a circulation stream into the mixer (not shown). The liquid raffinate (5) (principally an n-butane/n-butenes mixture) is supplied to the distillative drying K2 (in FIG. 3).

FIG. 2 shows a process variant of the extraction, in which the feedstock consists of a liquid substream (1*a*) and a gaseous substream (1*b*). The gaseous stream comprises, in addition to n-butane, n-butenes, small amounts of formic acid and possibly oxygen-containing $C_5$ compounds according to the partial pressures of the components, predominantly synthesis gas, i.e. carbon monoxide and hydrogen. As in FIG. 1, the liquid feed stream (1*a*) is supplied to the mixer M1 and mixed therein with the extraction alkali (2). The biphasic mixture (3) is supplied to the washer K1. In the washer, the gaseous feed stream (1*b*) is washed or extracted in countercurrent with the liquid mixture (3). The gaseous extract (5*a*), very substantially free of the troublesome impurities, is drawn off in the upper part of the washer K1 and supplied to the distillative drying K2 (in FIG. 3). The biphasic liquid stream (4) is drawn off in the lower part of the washer K1 and fed to the settler B1. In the settler B1, the phases are again separated, and the extract (6) is discharged as an aqueous phase laden with the impurities to be removed. A portion of the extract (6) can optionally be recycled back into the mixer as a circulation stream (not shown). The liquid raffinate (5*b*) is fed back to the distillative drying K2 (in FIG. 3). The lower part of the washer K1 can optionally also be configured such that the settler B1 is integrated into the washer K1 and the phases of liquid streams (5*b*) and (6) are separated in the washer (not shown).

FIG. 3 shows the distillative drying of the raffinate in column K2. The liquid raffinate stream (5) is, or the liquid raffinate stream (5*b*) and the gaseous raffinate stream (5*a*) are, introduced into the upper part of the distillation column K2. The vapours (7) of the column K2 are (partially) condensed (condenser not shown) and the resulting condensate is separated in vessel B2 into a gas phase (9), a liquid water phase (10) and a liquid organic phase (8). The gas phase (9) (principally synthesis gas) and the water phase (10) are discharged, while the organic phase (8) is recycled back into the upper part of the column K2. The bottom product (11) drawn off from column K2 is a virtually anhydrous hydrocarbon mixture, which is sent to the hydrogenation (in FIG. 4).

FIG. 4 shows the hydrogenation of the olefin stream and the distillative removal of the $C_5$ hydrocarbons. The olefins in stream (11) are hydrogenated in reactors R1 and R2. (The hydrogen supply to the hydrogenation reactors and the removal of offgas are not shown in FIG. 4.) The reactor output (13) is fed into the distillation column K3. The vapours (14) of column K3 are condensed (condenser not shown) and the resulting condensate is separated in vessel B3 into a gas phase and a liquid phase. The gas phase (15) consists predominantly of hydrogen and is discharged. The liquid phase consists of virtually pure n-butane. A portion of liquid phase is drawn off as target product in the form of stream (16), while the other portion (17) is conducted as reflux into column K3. The bottom product (18) obtained comprises small amounts of $C_5$ hydrocarbons and possibly traces of other high boilers.

The examples which follow are intended to illustrate the invention without restricting the range of application which is evident from the description and the claims.

EXAMPLE 1

Removal of Formic Acid by Alkali Extraction

Experimental Plant:

The studies of the removal of formic acid traces by alkali extraction or washing were conducted in a laboratory experimental plant which consisted essentially of a metering and extraction unit. The core of the laboratory plant was the extraction unit in the form of a jacketed stainless steel reactor of length 1.3 m and diameter 25 mm, which was filled completely with 3 mm glass beads. In order to improve the mixing of the organic phase with the aqueous sodium hydroxide solution, the reactor was provided with a circulation system. The circulation was ensured by a reaction mixing pump installed upstream of the reactor. The sodium hydroxide solution as the extraction or washing medium was metered directly into the reaction mixing pump. For the separation of the organic and aqueous phases downstream of the reactor, a 2 liter separation vessel was installed.

The reactant used was a butane/butene mixture containing 10% by mass of butenes, to which 500 ppm of formic acid had been added. The starting mixture was taken from a 30 l pressure reservoir and passed into the reactor with a Lewa pump. Just upstream of the reactor, CO was added to the starting mixture from the line by means of a mass flow meter. Downstream of the extraction unit, the mixture was passed into a 50 l product vat. A substream of the mixture was conducted into the 2 l separation vessel and analysed.

Experimental Procedure:

n-Butane/butene mixture with a formic acid content of 500 ppm was passed through the extraction unit (wash column) at three temperatures, 40, 60 and 80° C., at a throughput of 650 ml/h from the 30 l reservoir in the presence of sodium hydroxide solution and CO by means of a reaction pump.

The 25% sodium hydroxide solution used as the wash medium (70 ml/h) and the CO (500 ml (STP)/h) were fed directly to the reaction pump. After the phase separation, the organic phase was analysed and the residual formic acid content was determined. In two experiments, the $H_2O$ contents in the organic phase were additionally determined.

The volume ratio of the organic phase to aqueous phase in all experiments was about 10 to 1.

Results:

The results of the experiments regarding formic acid removal by washing are compiled in Table 1.

TABLE 1

Experimental results for removal of formic acid by means of alkali extraction.

| | | Experiment No. | | | |
|---|---|---|---|---|---|
| | Unit | 1 | 2 | 3 | 4 |
| Reactants: | | | | | |
| n-butane/butene | ml/h | 650 | 650 | 650 | 650 |
| HCOOH in $C_4$ HC | ppm | 500 | 500 | 500 | 500 |
| CO | ml/h | 500 | 500 | 500 | 500 |
| NaOH (25%) | ml/h | 70 | 70 | 70 | 70 |
| Temperature | ° C. | 42 | 60 | 70 | 80 |
| Pressure | bar | 20 | 20 | 20 | 20 |
| Circulation rate | l/h | 150 | 150 | 150 | 150 |
| Analysis: | | | | | |
| HCOOH | ppm | <5 ppm | <5 ppm | <5 ppm | <10 ppm |
| pH before | | 13.0 | 13.0 | 13.0 | 13.0 |
| pH after | | 12.9 | 13.0 | 13.0 | 13.0 |
| $H_2O$ in $C_4$ HC | ppm | 50 | 45 | 55 | 60 |

As can be inferred from Table 1 (experiments 1 to 4), the formic acid in the organic phase is virtually completely removed by the NaOH wash in the temperature range between 40 and 80° C. The formic acid contents of 500 ppm in the butane/butene mixture decline after the wash to residual contents of <5 ppm (detection limit of the analysis method used).

EXAMPLE 2

Hydrogenation of N-Butenes in the Presence of Formic Acid

A raffinate III from the applicant's $C_4$ line, which, in addition to the $C_4$ paraffins n-butane (72.3% by mass) and isobutane (0.1% by mass), contained about 27.6% by mass of n-butenes, was admixed with 100 ppm of formic acid and then hydrogenated in a laboratory circulation reactor. The catalyst used was a Pd-containing supported catalyst, H14814 from Degussa, containing 0.5% by mass of palladium on γ-alumina.

200 ml/h of reactant were passed over 5 g of catalyst at a temperature of 45° C. and a pressure of 12 bar, corresponding to an LHSV of about 27 $h^{-1}$. The LHSV (liquid hourly space velocity) serves as a measure of the catalyst loading. In the early stages of the experiment, after about 8 hours, an n-butene conversion of about 97.1% was determined. As the continuous hydrogenation continued, the conversion decreased gradually in the first 100 hours. After about 150 hours of experiment time, a steady state with a conversion of about 86.7% was attained. These conversion values remained constant until completion of the experiment after 500 hours.

EXAMPLE 3

Hydrogenation of N-Butenes without Formic Acid

A raffinate III of the same composition as in example 2 but without traces of formic acid was hydrogenated in a laboratory circulation reactor under the same reaction conditions (same catalyst, throughput, temperature and pressure) as in example 2.

Under the selected conditions, after a startup phase of about 50 hours of experiment time, a steady state conversion of 97.8%, corresponding to a residual content of n-butenes of 0.6% by mass, was determined. This high conversion remained constant until completion of the experiment after 500 hours.

A comparison of the n-butene conversions with and without formic acid in the reactant shows that a distinct decline in the conversion to a constant value is detected in the presence of formic acid.

The invention claimed is:

1. A process for preparing low-odor n-butane, the process comprising:
    mixing a n-butane feedstock with an aqueous solution comprising an alkali metal hydroxide or an alkaline earth metal hydroxide to obtain a biphasic mixture;
    allowing the biphasic mixture to separate into an aqueous phase comprising a formate salt of the alkali metal or alkaline earth metal and an n-butane phase consisting essentially of n-butane, n-butenes and water;
    separating the aqueous phase from the n-butane phase;
    removing the water from the n-butane phase to obtain an anhydrous mixture of n-butane and n-butenes; and
    catalytically hydrogenating the anhydrous mixture to obtain the low odor n-butane;
    wherein
    a temperature of the biphasic mixture is from 15 to 120° C., and
    wherein
    the n-butane feedstock comprises n-butene, carbon monoxide, and formic acid in a content of from 0.001 to 1% by mass, and
    a content of the alkali metal hydroxide or alkaline earth metal hydroxide in the aqueous solution is from 0.5 to 30% by mass.

2. The process of claim 1,
    wherein the aqueous solution comprises sodium hydroxide in a concentration of from 0.5 to 2.5% by mass.

3. The process of claim 1,
    wherein a pressure of the mixing and separation is from 0.5 to 5 MPa.

4. The process of claim 1,
    wherein a proportion of carbon monoxide in the n-butane feedstock is from 1 to 10% by mass.

5. The process of claim 1,
    wherein the n-butane feedstock further comprises hydrogen.

6. The process of claim 1,
    wherein the mixing and separation comprises extracting in a mixer-settler unit.

7. The process of claim 6,
    wherein the mixer-settler unit is a static mixer.

8. The process of claim 6,
    wherein the mixer-settler unit is a pump.

9. The process of claim 1,
    wherein the mixing and separation comprises extracting in an extraction column.

10. The process of claim 1,
    wherein the extracted mixture is entirely or partly liquid.

11. The process of claim 1,
    wherein catalytically hydrogenating the anhydrous mixture comprises hydrogenating in a liquid phase over a palladium catalyst at a temperature of from 20 to 140° C. and at a pressure of from 0.6 to 3 MPa.

12. The process of claim 1, wherein removing the water comprises distillation.

13. The process of claim 1,
    further comprising dewatering the low odor n-butane by distillation, to obtain a dewatered output.

14. The process of claim 1,
    further comprising removing $C_5$ hydrocarbons from the n-butane phase or the low-odor n-butane by distillation.

15. The process of claim 1,
    wherein the n-butane feedstock is a stream from a $C_4$ hydroformylation.

16. The process of claim 4, wherein the proportion of carbon monoxide in the n-butane feedstock is from 2 to 7% by mass.

17. The process of claim 8, wherein the mixer-settler unit is a centrifugal pump.

18. The process of claim 1, wherein a content of linear butane in the n-butane feedstock is below 30% by mass.

19. The process of claim 1, wherein the aqueous solution is a sodium hydroxide solution, a potassium hydroxide solution, or both.

20. The process of claim 13, further comprising removing $C_5$ hydrocarbons from the low-odor n-butane or the dewatered output by distillation.

* * * * *